United States Patent [19]

McClelland et al.

[11] Patent Number: 5,821,341
[45] Date of Patent: Oct. 13, 1998

[54] ANTIBODIES TO SICAM-1

[75] Inventors: Alan McClelland, Old Saybrook; Jeffrey M. Greve, Branford, both of Conn.

[73] Assignee: Bayer Corporation, West Haven, Conn.

[21] Appl. No.: 443,965

[22] Filed: May 18, 1995

Related U.S. Application Data

[62] Division of Ser. No. 425,989, Apr. 20, 1995, which is a continuation of Ser. No. 156,653, Nov. 22, 1993, abandoned, which is a continuation of Ser. No. 5,204, Jan. 15, 1993, abandoned, which is a continuation of Ser. No. 449,356, Dec. 21, 1989, abandoned, which is a continuation-in-part of Ser. No. 445,951, Dec. 13, 1989, abandoned, which is a continuation-in-part of Ser. No. 301,192, Jan. 24, 1989, Pat. No. 5,235,049.

[51] Int. Cl.$^6$ ..................................................... C07K 16/24
[52] U.S. Cl. .................. 530/388.22; 530/387.1; 530/387.9; 530/388.1; 530/389.6
[58] Field of Search .............................. 530/387.1, 387.9, 530/388.1, 388.22, 388.7, 388.73, 389.6

[56] References Cited

U.S. PATENT DOCUMENTS 5,235,049   8/1993   McClelland et al. .

*Primary Examiner*—Lila Feisee
*Assistant Examiner*—Phillip Gambel

[57] ABSTRACT

The present invention relates to a soluble form of intercellular adhesion molecule (sICAM-1) and purified and isolated human sICAM-1, and antibodies thereto. This invention also relates to a purified and isolated DNA sequence encoding sICAM-1. The extracellular domain of sICAM-1 and insoluble ICAM-1 are substantially the same. ICAM-1 is involved in the process through which lymphocytes attach to cellular substrates during inflammation and serves as the major human rhinovirus receptor (HRR). sICAM-1 therefore has both the property of reducing immune inflammation and inhibiting infection of rhinovirus and Coxsackie A virus.

4 Claims, 8 Drawing Sheets

| | | |
|---|---|---|
| 58 | ATGGCTCCCAGCAGCCCCGGCCCGCGCTGCCCGCACTCCTGGTCCTGCTCGGGGCTCTG | 117 |
| | M A P S S P R P A L P A L L V L L G A L | |

| | | |
|---|---|---|
| 118 | TTCCCAGGACCTGGCAATGCCCAGACATCTGTGTCCCCCTCAAAAGTCATCCTGCCCCGG | 177 |
| | F P G P G N A Q T S V S P S K V I L P R | 13 |

| | | |
|---|---|---|
| 178 | GGAGGCTCCGTGCTGGTGACATGCAGCACCTCCTGTGACCAGCCCAAGTTGTTGGGCATA | 237 |
| | G G S V L V T C S T S C D Q P K L L G I | 33 |

| | | |
|---|---|---|
| 238 | GAGACCCCGTTGCCTAAAAAGGAGTTGCTCCTGCCTGGGAACAACCGGAAGGTGTATGAA | 297 |
| | E T P L P K K E L L L P G N N R K V Y E | 53 |

| | | |
|---|---|---|
| 298 | CTGAGCAATGTGCAAGAAGATAGCCAACCAATGTGCTATTCAAACTGCCCTGATGGGCAG | 357 |
| | L S N V Q E D S Q P M C Y S N C P D G Q | 73 |

| | | |
|---|---|---|
| 358 | TCAACAGCTAAAACCTTCCTCACCGTGTACTGGACTCCAGAACGGGTGGAACTGGCACCC | 417 |
| | S T A K T F L T V Y W T P E R V E L A P | 93 |

| | | |
|---|---|---|
| 418 | CTCCCCTCTTGGCAGCCAGTGGGCAAGAACCTTACCCTACGCTGCCAGGTGGAGGGTGGG | 477 |
| | L P S W Q P V G K N L T L R C Q V E G G | 113 |

| | | |
|---|---|---|
| 478 | GCACCCCGGGCCAACCTCACCGTGGTGCTGCTCCGTGGGGAGAAGGAGCTGAAACGGGAG | 537 |
| | A P R A N L T V V L L R G E K E L K R E | 133 |

| | | |
|---|---|---|
| 538 | CCAGCTGTGGGGGAGCCCGCTGAGGTCACGACCACGGTGCTGGTGAGGAGAGATCACCAT | 597 |
| | P A V G E P A E V T T T V L V R R D H H | 153 |

| | | |
|---|---|---|
| 598 | GGAGCCAATTTCTCGTGCCGCACTGAACTGGACCTGCGGCCCCAAGGGCTGGAGCTGTTT | 657 |
| | G A N F S C R T E L D L R P Q G L E L F | 173 |

| | | |
|---|---|---|
| 658 | GAGAACACCTCGGCCCCCTACCAGCTCCAGACCTTTGTCCTGCCAGCGACTCCCCCACAA | 717 |
| | E N T S A P Y Q L Q T F V L P A T P P Q | 193 |

| | | |
|---|---|---|
| 718 | CTTGTCAGCCCCCGGGTCCTAGAGGTGGACACGCAGGGGACCGTGGTCTGTTCCCTGGAC | 777 |
| | L V S P R V L E V D T Q G T V V C S L D | 213 |

| | | |
|---|---|---|
| 778 | GGGCTGTTCCCAGTCTCGGAGGCCCAGGTCCACCTGGCACTGGGGGACCAGAGGTTGAAC | 837 |
| | G L F P V S E A Q V H L A L G D Q R L N | 233 |

FIG. 1A [SEQ ID NO: 10]

```
838   CCCACAGTCACCTATGGCAACGACTCCTTCTCGGCCAAGGCCTCAGTCAGTGTGACCGCA   897
       P  T  V  T  Y  G  N  D  S  F  S  A  K  A  S  V  S  V  T  A    253

898   GAGGACGAGGGCACCCAGCGGCTGACGTGTGCAGTAATACTGGGGAACCAGAGCCAGGAG   957
       E  D  E  G  T  Q  R  L  T  C  A  V  I  L  G  N  Q  S  Q  E    273

958   ACACTGCAGACAGTGACCATCTACAGCTTTCCGGCGCCCAACGTGATTCTGACGAAGCCA   1017
       T  L  Q  T  V  T  I  Y  S  F  P  A  P  N  V  I  L  T  K  P    293

1018  GAGGTCTCAGAAGGGACCGAGGTGACAGTGAAGTGTGAGGCCCACCCTAGAGCCAAGGTG   1077
       E  V  S  E  G  T  E  V  T  V  K  C  E  A  H  P  R  A  K  V    313

1078  ACGCTGAATGGGGTTCCAGCCCAGCCACTGGGCCCGAGGGCCCAGCTCCTGCTGAAGGCC   1137
       T  L  N  G  V  P  A  Q  P  L  G  P  R  A  Q  L  L  L  K  A    333

1138  ACCCCAGAGGACAACGGGCGCAGCTTCTCCTGCTCTGCAACCCTGGAGGTGGCCGGCCAG   1197
       T  P  E  D  N  G  R  S  F  S  C  S  A  T  L  E  V  A  G  Q    353

1198  CTTATACACAAGAACCAGACCCGGGAGCTTCGTGTCCTGTATGGCCCCCGACTGGACGAG   1257
       L  I  H  K  N  Q  T  R  E  L  R  V  L  Y  G  P  R  L  D  E    373

1258  AGGGATTGTCCGGGAAACTGGACGTGGCCAGAAAATTCCCAGCAGACTCCAATGTGCCAG   1317
       R  D  C  P  G  N  W  T  W  P  E  N  S  Q  Q  T  P  M  C  Q    393

1318  GCTTGGGGGAACCCATTGCCCGAGCTCAAGTGTCTAAAGGATGGCACTTTCCCACTGCCC   1377
       A  W  G  N  P  L  P  E  L  K  C  L  K  D  G  T  F  P  L  P    413

1378  ATCGGGGAATCAGTGACTGTCACTCGAGATCTTGAGGGCACCTACCTCTGTCGGGCCAGG   1437
       I  G  E  S  V  T  V  T  R  D  L  E  G  T  Y  L  C  R  A  R    433

1438  AGCACTCAAGGGGAGGTCACCCGCAAGCCCCCGGTATGAGATTGTCATCATCACTGTGG   1497
       S  T  Q  G  E  V  T  R  K  P  P  G  M  R  L  S  S  S  L  W    453

1498  TAG  1500
       *
```

FIG. 1B [SEQ ID NO: 10] (con't)

COMPARISON OF C-TERMINAL REGIONS OF ICAM-1 AND sICAM-1

```
1441  ACTCAAGGGGAGGTCACCCGCAAGGTGACCGTGAATGTGCTCTCCCCCCGGTATGAGATT
 435  T  Q  G  E  V  T  R  K  V  T  V  N  V  L  S  P  R  Y  E  I

1441  ACTCAAGGGGAGGTCACCCGCAAG-------------------CCCCCCGGTATGAGATT
 435  T  Q  G  E  V  T  R  K                       P  P  G  M  R  L

1501  GTCATCATCACTGTGGTAGCAGCCGCAGTCATAATGGGCACTGCAGGCCTCAGCACGTAC
 455  V  I  I  T  V  V  A  A  A  V  I  M  G  T  A  G  L  S  T  Y

1482  GTCATCATCACTGTGGTAGCAGCCGCAGTCATAATGGGCACTGCAGGCCTCAGCACGTAC
 449   S  S  S  L  W  *

1561  CTCTATAACCGCCAGCGGAAGATCAAGAAATACAGACTACAACAGGCCCAAAAAGGGACC
 475  L  Y  N  R  Q  R  K  I  K  K  Y  R  L  Q  Q  A  Q  K  G  T

1542  CTCTATAACCGCCAGCGGAAGATCAAGAAATACAGACTACAACAGGCCCAAAAAGGGACC

1621  CCCATGAAACCGAACACACAAGCCACGCCTCCCTGAACCTATCCCGGGACAGGGCCTCTT
 495  P  M  K  P  N  T  Q  A  T  P  P  *

1602  CCCATGAAACCGAACACACAAGCCACGCCTCCCTGAACCTATCCCGGGACAGGGCCTCTT
```

UPPER LINES: ICAM-1 cDNA SEQUENCE AND TRANSLATION [SEQ ID NO: 11]

LOWER LINES: sICAM-1 cDNA SEQUENCE AND TRANSLATION [SEQ ID NO: 12]

FIG.2

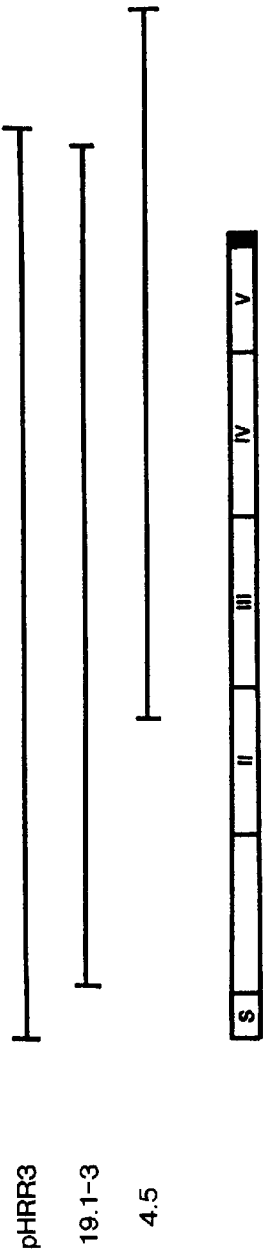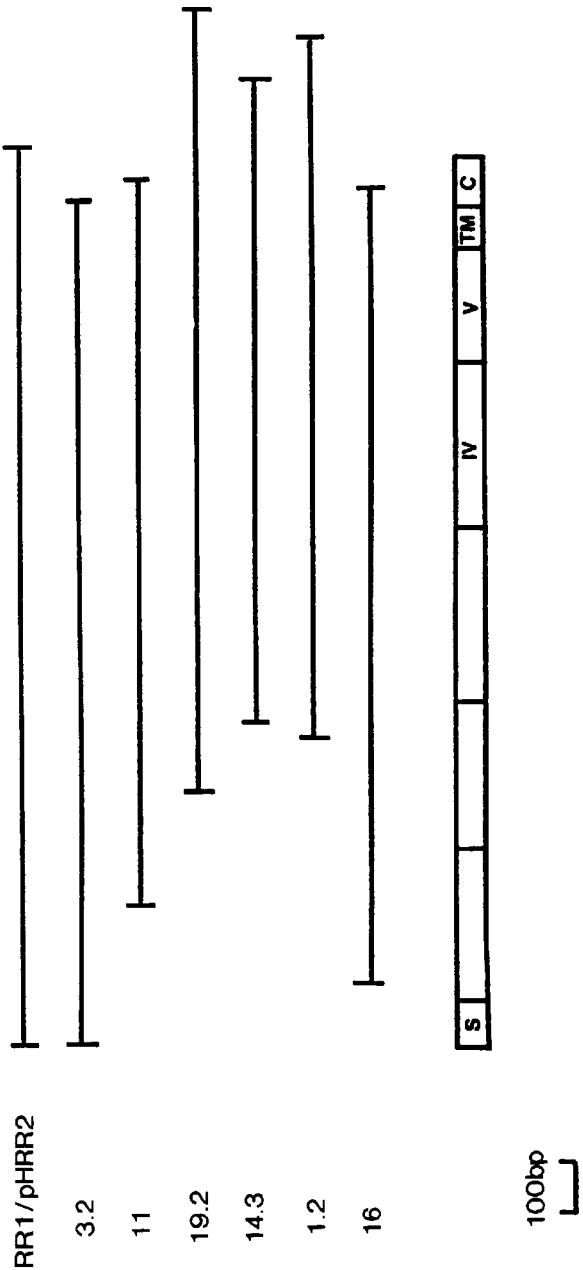

ANTIBODIES TO SICAM-1

This is a divisional of copending application U.S. Ser. No. 08/425,989 filed Apr. 20, 1995, which is a continuation of U.S. Ser. No. 08/156,653 filed Nov. 22, 1993, now abandoned, which is a continuation of U.S. Ser. No. 08/005,204 filed Jan. 15, 1993, now abandoned, which is a continuation of U.S. Ser. No. 07/449,356 filed Dec. 21, 1989, now abandoned, which is a continuation-in-part of U.S. Ser. No. 07/445,951 filed Dec. 13, 1989, now abandoned, which is a continuation-in-part of U.S. Ser. No. 07/301,192 filed Jan. 24, 1989, which issued as U.S. Pat. No. 5,235,049 on Aug. 10, 1993.

BACKGROUND OF THE INVENTION

The present invention relates to a soluble form of intercellular adhesion molecule (sICAM-1) as well as the DNA sequence encoding sICAM-l. sICAM-1 and ICAM-1 have substantial similarity, in that they share the first 442 $NH_2$-terminal amino acids of the extracellular domain. However, sICAM-1 differs from ICAM-1 at the C-terminus, and these changes confer solubility to sICAM-1. ICAM-1 is known to mediate adhesion of many cell types, including endothelial cells, to lymphocytes which express lymphocyte function-associated antigen-1 (LFA-1). ICAM-1 has the property of directly binding LFA-1. There is also evidence for LFA-1 mediated adhesion which is not via ICAM-1. Additionally, ICAM-1 has the ability to bind both LFA-1 and human rhinovirus. It has the property of inhibiting infection of rhinovirus and Coxsackie A viruses. It may be used to antagonize adhesion of cells mediated by ICAM-1 binding including ICAM-1/LFA-1 binding and thus be useful in treatment of inflammation, graft rejection,-LFA-1 expressing tumors, and other processes involving cell adhesion. Based on the substantial similarity of the extracellular domains of ICAM-1 and sICAM-1, sICAM-1 has the properties identified for ICAM-1.

The major Human Rhinovirus Receptor (HRR) has been transfected, identified, purified and reconstituted as described in co-pending U.S. patent applications Ser. Nos. 262570 and 262428 filed Oct. 25, 1988. This receptor has been shown to be identical to a previously described cell surface protein, ICAM-1. European Patent Application 0 289 949 describes a membrane associated cell adhesion molecule (ICAM-1) which mediates attachment of many cell types including endothelial cells to lymphocytes which contain LFA-1. This patent application provides a discussion of the present research in the field of intercellular adhesion molecules. It is important to note that the inventors specifically looked for an alternatively spliced MRNA for ICAM-1 and did not identify one. ICAM-1 was first identified based on its role in adhesion of leukocytes to T-cells (Rothlein, R. et al. *J. Immunol.* 137: 1270–1274 (1986)) which has been shown to be mediated by the heterotypic binding of ICAM-1 to LFA-1 (Marlin et al. *Cell* 51: 813–819 (1987)). The primary structure of ICAM-1 has revealed that it is homologous to the cellular adhesion molecules Neural Cell Adhesion Molecule (NCAM) and Mylein-Associated Glycoprotein (MAG), and has led to the proposal that it is a member of the immunoglobulin supergene family (Simmons et al. *Nature* 331: 624–627 (1988); Staunton et al, *Cell* 52: 925–933 (1988) The DNA sequence of cDNA clones are described in the above referenced papers by Simmons et al and Staunton et al. supra, from which the amino acid sequence of ICAM-1 can be deduced. The ICAM-1 molecule has a typical hydrophobic membrane spanning region containing 24 amino acids and a short cytoplasmic tail containing 28 amino acids. The ICAM-1 of the prior art is an insoluble molecule which is solubilized from cell membranes by lysing the cells in a non-ionic detergent. The solubilized ICAM-1 mixture in detergent is then passed through a column matrix material and then through a monoclonal antibody column matrix for purification.

SUMMARY OF THE INVENTION

The present invention provides an endogenous alternatively spliced molecular species of ICAM-1 designated sICAM-1 which displays an alternative MRNA sequence and which is soluble without the addition of a detergent.

The present invention provides purified and isolated human soluble intercellular adhesion molecule (sICAM-1), or a functional derivative thereof, substantially free of natural contaminants. sICAM-l can be obtained from HeLa, HE1 and primary transfectant cells thereof characterized by being soluble in the absence of nonionic detergents and being the translation product defined by a novel mRNA sequence. This natural product of human cells has the advantage of being secreted from cells in a soluble form and not being immunogenic. The natural soluble product differs from the natural insoluble product in that the soluble product contains a novel sequence of 11 amino acid residues at the C-terminus and does not contain the membrane spanning and cytoplasmic domains present in the insoluble form.

The present invention provides a purified and isolated DNA sequence encoding sICAM-1 as well as a host cell encoding said sequence.

The present invention provides a method of recovering soluble intercellular adhesion molecule in substantially pure form comprising the steps of:

(a) removing the supernatant from unlysed cells, (b) introducing the supernatant to an affinity matrix containing immobilized antibody capable of binding to sICAM-1, (c) permitting said sICAM-1 to bind to said antibody of said matrix, (d) washing said matrix to remove unbound contaminants, and (e) recovering said sICAM-1 in substantially pure form by eluting said sICAM-1 from said matrix.

Further purification utilizing a lectin or wheat germ agglutinin column may be used before or after the antibody matrix step. Other purification steps could include sizing chromatography, ion chromatography, and gel electrophoresis. Further purification by velocity sedimentation through sucrose gradients may be used. The antibody capable of binding to sICAM-1 could include antibodies against ICAM-1 or HRR.

The present invention includes polyclonal antibodies against sICAM-1.

The present invention further includes an antibody specific for sICAM-1, capable of binding to the sICAM-1 molecule and that is not capable of binding to ICAM-1. For a method for producing a peptide antisera see Green et al, Cell 28: 477–487 (1982).

The invention also includes a hybridoma cell line capable of producing such an antibody.

This invention further includes the therapeutic use of antibodies specifically directed to sICAM-1 to increase the adhesion of cells mediated by ICAM-1 and LFA-1.

The invention further includes a method for producing an antibody which is capable of binding to sICAM-1 and not to ICAM-1 comprising the steps of (a) preparing a peptide-protein conjugate said peptide-protein conjugate specific to at least a portion of the unique 11 amino acid seuqence present in sICAM-1, (b) immunizing an animal with said peptide-protein conjugate, (c) boosting the animals, and (d) obtaining the antisera.

The antibodies would be capable of binding to sICAM-1 and not capable of binding to ICAM-1. The invention includes the hybridoma cell line which produces an antibody of the same specificity, the antibody produced by the hybridoma cell and the method of production.

The invention further includes a method of inhibiting lymphocyte function associated antigen (LFA-1) and intercellular adhesion molecule-1 (ICAM-1) interaction comprising the step of contacting LFA-1 containing cells with sICAM-1 or a functional derivative thereof. This method of inhibition of ICAM-1 adhesion has application in such disease states as inflammation, graft rejection, and for LFA-1 expressing tumor cells.

This invention further includes a method of diagnosis of the presence and location of an LFA-1 expressing tumor cell.

This invention further includes a method for substantially reducing the infection of human rhinoviruses of the major receptor group comprising the step of contacting the virus with sICAM-1 or a functional derivative thereof.

BRIEF DESCRIPTION OF THE DRAWINGS

FIG. 1, parts A and B, shows the nucleotide and amino acid sequence of sICAM-1.

FIG. 2 is a comparision of the C-terminal regions of sICAM-1 and ICAM-1. The nucleotide and deduced amino acid sequences of ICAM-1 and sICAM-1 are shown beginning at amino acid residue 435. Dashes in the sICAM-1 sequence indicate missing nucleotides. The positions of the stop codons in both proteins are indicated by an asterisk.

FIG. 4A: Southern blot of HeLa (Lane 1), LTK$^-$ (Lane 2) and HE1 (Lane 3) DNA restricted with Eco R1 and probed with the oligonucleotide ICAM-1.

FIG. 7A and B are a graphical representation of the cloned sICAM-1 and ICAM-1 plasmids.

FIG. 7A. pHRR3 is a full length cDNA encoding sICAM-1 obtained by PCR. Clones 19.1-3 and 4.5 are partial cDNA clones encoding sICAM-1 obtained from an HE1 cDNA library in lambda GT11. Beneath the clones is a schematic of the sICAM-1 molecule. S denotes the signal peptide and I to V the IgG homologous domains. The solid box indicates the unique 11 amino acid C-terminus.

FIG. 7B pHRR1 and pHRR2 are full length ICAM-1 cDNA clones obtained by PCR. The remaining ICAM-1 clones were obtained from an HE1 cDNA library in lambda GT11. Beneath the clones is a schematic of the ICAM-1 molecule, showing the signal peptide (S), the five IgG homologous domains (I to V), the transmembrane region (TM) and the cytoplasmic domain (C).

DESCRIPTION OF THE PREFERRED EMBODIMENTS

Figure 3A:
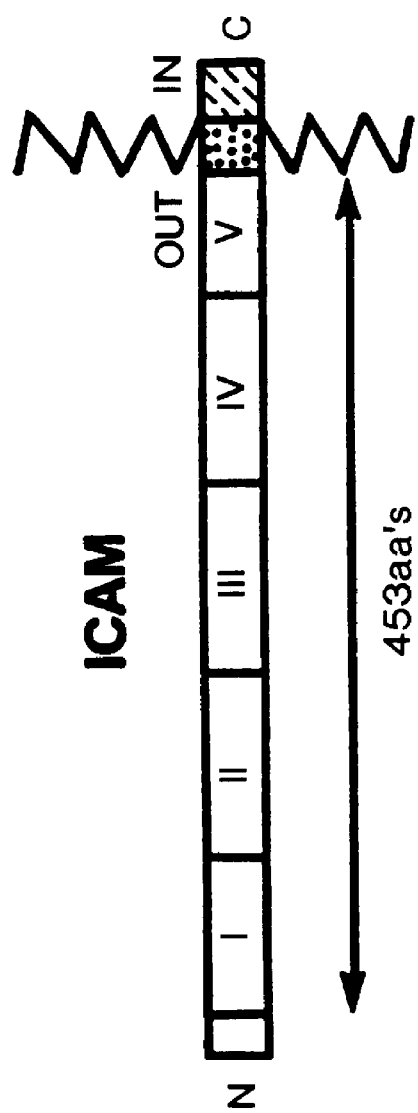
FIG. 3A and B are a comparison of the structure of sICAM-1 and ICAM-1. The membrane spanning region of ICAM-1 is indicated by the stippled box and the cytoplasmic domain by the hatched box. The novel C-terminus of sICAM-1 is indicated by the solid box. The five predicted domains showing homology with immunoglobulin are numbered I to V.

One aspect of the present invention relates to the discovery of a soluble natural binding ligand to the receptor binding site of Human Rhinovirus (HRV) and which also binds to LFA-1. This soluble natural molecule is related to but distinct from the molecule designated "Intercellular Adhesion Molecule-1" or "ICAM-1" which is insoluble, bound to the cell membrane and possesses a typical hydrophobic membrane spanning region and a short cytoplasmic tail. The novel protein of the present invention has a DNA sequence which includes a significant difference from the published DNA sequence for ICAM-1. sICAM-1 contains most of the extracellular domain of ICAM-1, which includes the functional domains for multiple functions including HRV and LFA-1 binding, but lacks the membrane spanning and cytoplasmic domains. sICAM-1 retains the ability to bind HRV and LFA-1 and is secreted in a soluble form. The DNA sequence for sICAM-1 contains a deletion of 19 base pairs from nucleotide 1465 to 1483 according to the numbering of Staunton et al, supra (1988). The remainder of the sICAM-1 clone matches the published ICAM-1 sequence with the exception of a substitution of an A for G at nucleotide position 1462 which changes Glu 442 to Lys, as shown in FIG. 1. The sequence of amino acid residues in a peptide is designated in accordance with standard nomenclature such as Lehninger's *Biochemistry*, Worth Publishers, New York, N.Y. (1970). sICAM-1 is a natural product of HeLa and HE1 cells and other human cells which should have the property of binding to and inhibiting the infection of human rhinovirus and Coxsackie A viruses. It also has the property of binding to LFA-1 and may be used to antagonize adhesion of cells mediated by ICAM-1/LFA-1 binding and thus be useful as a therapeutic in treatment of inflammation, graft rejection, suppression of LFA-1 expressing tumor cells and other processes involving cell adhesion. Isolated and purified sICAM-1 protein as a therapeutic would not possess the immunogenic problems associated with foreign proteins. The secretion of a soluble naturally occurring protein eliminates the problems associated with production and purification of an insoluble, cell membrane bound protein, since cell lysis is not required and thus continuous culture can be employed as well as simplified procedures for purification and isolation of sICAM-1.

Non-human mammalian cell lines which express the major human rhinovirus receptor gene have been previously identified and are the subject matter of copending U.S. patent application No. 262570 and 262428 filed Oct. 25, 1988, and include references to the ATCC deposits for the cell lines. The major human rhinovirus receptor was identified with monoclonal antibodies which inhibit rhinovirus infection. These monoclonal antibodies recognized a 95 kd cell surface glycoprotein on human cells and on mouse transfectants expressing a rhinovirus-binding phenotype. Purified 95 Kd protein binds to rhinovirus in vitro. Protein sequence from the 95 kd protein showed an identity with that of ICAM-1; a cDNA clone obtained from mouse transfectants expressing the rhinovirus receptor had the same sequence published for ICAM-1, except for the A for G change previously described. Thus it was determined that the major human rhinovirus receptor and ICAM-1 were the same protein. A transfected mouse L-cell line designated HE1 had been isolated which contained and expressed the HRR gene or ICAM-1 gene. The ICAM-1 terminology has been used although it is now recognized that HRR and ICAM-1 are interchangeable.

A randomly primed cDNA library was prepared in lambda GT11 from HE1 polyA+ RNA. The library was screened in duplicate using two oligonucleotides derived from the published sequence of ICAM-1. Oligonucleotide ICAM-1 has the sequence GAGGTGTTCTCAAACAGCTCCAGCCCT-TGGGGCCGCAGGTCCAGTTC SEQ ID NO: 5 and oligonucleotide ICAM-3 has the sequence CGTTGGCAGGA-CAAAGGTCTGGAGCTGGTAGGGGGCCGAGGTGTTCT SEQ ID NO: 6.

Figure 4A:
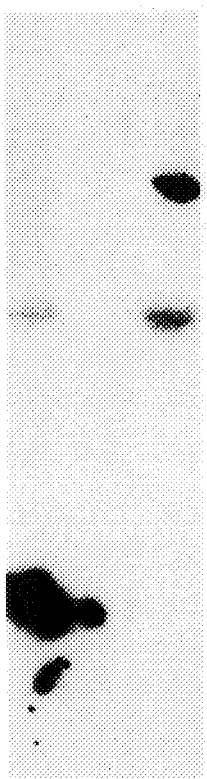
FIG. 4A, B and C show the ICAM-1 gene and its expression in HRR transfectants.
Figure 4B:
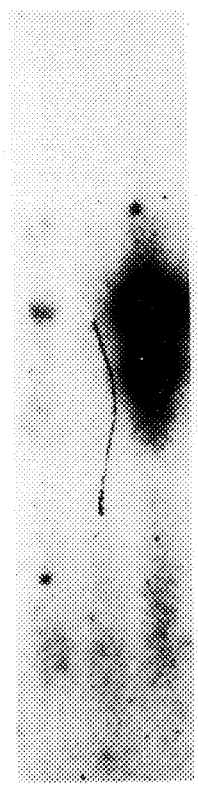
FIG. 4B: Northern blot of HeLa (Lane 1), Lkt$^-$ (Lane 2), and HE1 (Lane 3). poly A+ RNA probed with the oligonucleotide ICAM-1.
Figure 4C:
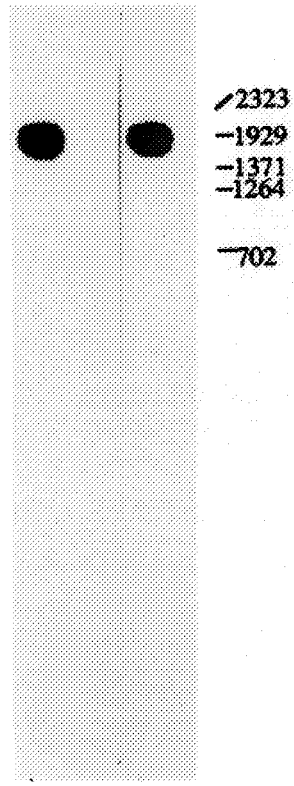
FIG. 4C: PCR amplification of cDNA prepared from HeLa (Lane 1), Ltk$^-$ (Lane 2) and HE1 (Lane 3) poly A+ RNA. The primers used were from the N-terminal and C-terminal coding regions of ICAM-1 having the sequence ggaattcATGGCTCCCAGCAGCCCCCG-GCCC SEQ ID NO: 1 and ggaattcTCAGGGAGGCGTG-GCTTGTGTGTT SEQ. ID NO: 2. Upper case denotes ICAM-1 sequence, lower case restriction site linkers. Lanes 1 and 2, 72 hour exposure, Lane 3, 90 minute exposure.
Figure 5:
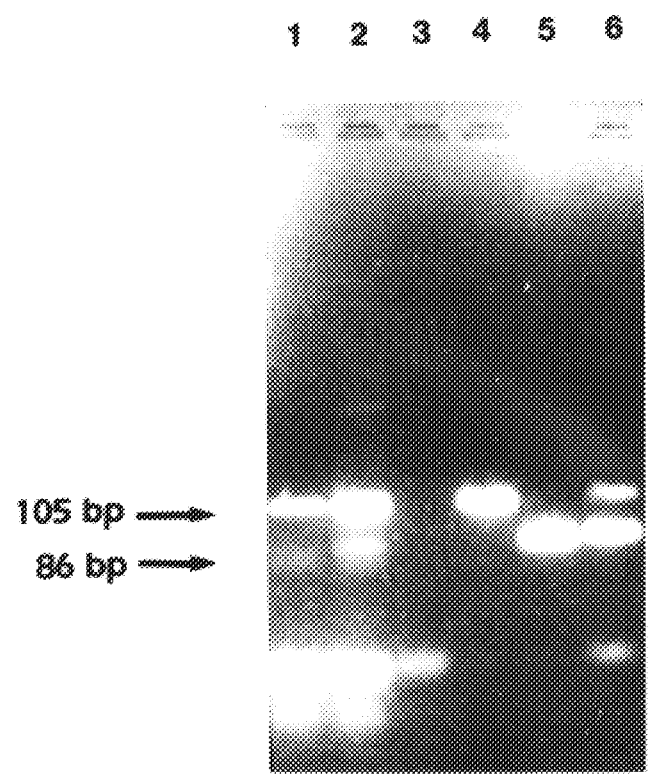
FIG. 5 is a gel showing the detection of the ICAM-1 and sICAM-1 mRNAs in HeLa and HE1 cells. PCR amplification was performed on 100 ng single stranded cDNA using the primers PCR 5.4 (CTTGAGGGCACCTACCTCTGTCGG) SEQ ID NO: 3 and PCR 3.4 (AGTGATGATGACAATCTCATACCG) SEQ ID NO: 4. Extensions were performed at 72 C for 25 cycles and one tenth of the product was analysed on a 1% agarose/3% NuSieve® gel FMC Rockland, Me. Lane 1, HeLa cDNA; lane 2, HE1 cDNA; lane 3, LTK$^-$ cDNA; lane 4, ICAM-1 phage control;, lane 5, sICAM-1 phage control; lane 6, ICAM-1+sICAM-1 phage control. Specific amplification products of 105 bp and 86 bp are indicated by the arrows.
Figure 6:
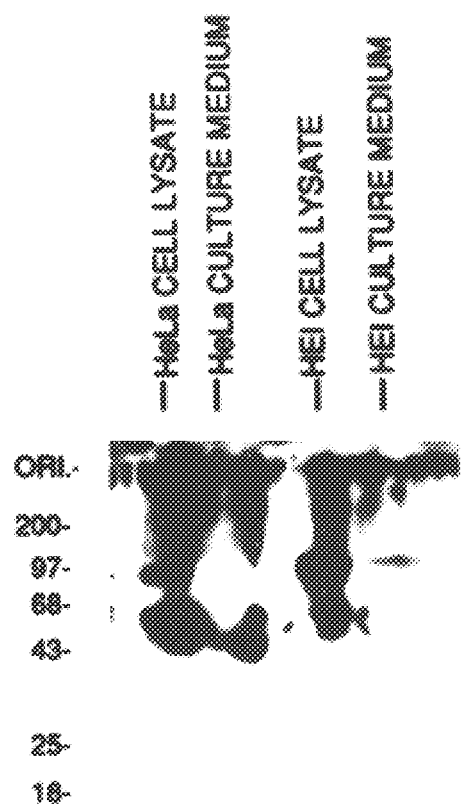
FIG. 6 is a Western blot showing the synthesis of a soluble form of ICAM-1 protein by HeLa and HE1 cells. It demonstrates the existence of a protein species in the culture supernatant of HeLa and HE1 cells related to ICAM-1. Equivalent aliquots of cell lysates and culture supernatants were separated by SDS-PAGE, blotted onto nitrocellulose, and probed with a rabbit polyclonal antisera to ICAM-1 followed by $^{125}$I protein A; a species migrating close to the position of membrane-bound ICAM-1 is seen in both HeLa and HE1 culture supernatants.

Eight positive clones were obtained from one screen and three were selected for further study. DNA sequencing of two of the clones showed identity with the published ICAM-1 sequence. The sequence of the third clone, lambda 19.1-3 was significantly different from the other two clones in that there was a deletion of 19 bp from nucleotide 1465 to 1483 according to the numbering of Staunton et al, supra. The 19 bp deletion was present in a second cDNA, lambda HE1-4.5 and independently confirmed using polymerase chain reaction (PCR) generated cDNA. Analysis of the cDNA sequence predicted the existence of a secreted form of ICAM-1 that is generated by an alternative splicing mechanism. Western blot identification of sICAM-1 from culture supernatants of HE1 and HeLa cell lines confirm that the sICAM-1 mRNA sequence encodes a soluble form of ICAM-1 that does not associate with the cell surface but is released into the cell medium. An alternatively spliced mRNA generating a secreted form of another adhesion molecule (NCAM) has been identified (Glower et al, Cell 55:955–964 (1988)), although in NCAM an exon is incorporated into the mRNA while in the present invention an exon is deleted from the mRNA. No alternative MRNA sequence for ICAM-1 had previously been identified. (Staunton et al.) sICAM-1 cDNA Clones A randomly primed cDNA library was constructed in lambda GT11 from HE1 poly A+ by Clontech Laboratories, Palo Alto, Calif. The library was screened with two 47 mer oligonucleotide probes from the middle of the ICAM-1 coding sequence. A positive clone designated 19.1-3 was isolated which had an insert of 1.5 kb; a second cDNA clone designated 4.5 which has an insert of 1.25 kb was isolated; and an additional cDNA clone pHRR-3 was obtained by subcloning the products of PCR amplification into Bluescript® utilizing the Perkin-Elmer/Cetus DNA Amplification System, Perkin Elmer, Wellesley Mass., as shown in FIG. 4C, lane 3. These clones showed a significant difference from the published ICAM-1 sequence. They all contain a deletion of 19 base pairs from nucleotide 1465 to 1483 according to the numbering of Staunton et al. supra. In order to demonstrate directly that the s-ICAM mRNA is present in HE1 cells and HeLa cels, a PCR experiment was performed using primers which flank the 19 bp region which is absent from the s-ICAM MRNA (FIG. 8). Using these primers the product from the ICAM-1 mRNA is 105 bp while the s-ICAM-1 product is 19 bp shorter i.e. 86 bp. This experiment shows that both HE1 cells and HeLa cells contain both forms of the ICAM-1mRNA while the control L-cells do not. A synthetic oligonucleotide designated PCR3.2 having the following sequence:

ggaattcTCACTCATACCGGGGGGAGAGCACATT [SEQ ID NO: 7]

was used to distinguish between cDNA clones containing the 19 bp deletion from clones not containing the 19 bp deletion. The synthetic oligonucleotide does not bind to cDNA clones which contain the 19 bp deletion. In addition, partial sequence of the cDNA 19.1-3 and PHRR-3 confirmed the 19 bp deletion. This data indicates that there are at least two different and distinct ICAM-1 species in HE1 cells. The insoluble ICAM-1 of the prior art and a novel soluble form as described in the present invention.

Figure 3B:
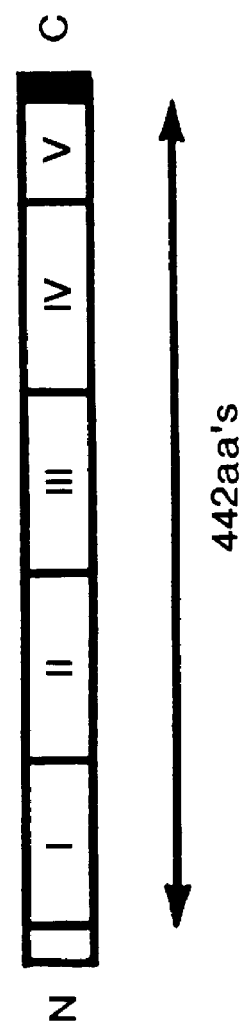

The sequences of the deleted (sICAM-1) and the nondeleted (ICAM-1) forms of the Intercellular Adhesion Molecule-1 mRNA represented by the cDNA clones are shown in FIG. 2. The sequence at the point of deletion is AGGT consistent with an RNA splice junction. The removal of 19 bases from the mRNA shifts the reading frame and causes the two polypeptide sequences to diverge at amino acid residue 443. The deleted form (sICAM-1) contains an additional 11 residues followed by an in-frame termination codon. This molecule thus consists of 453 amino acids as compared to 505 amino acids for the nondeleted form. Beginning with the N-terminus of ICAM-1, sICAM-1 has 442 amino acids in common with ICAM-1. The deleted form (sICAM-1) contains a unique 11 amino acid C-terminus but lacks the membrane spanning (24 amino acids) and cytoplasmic tail 28 amino acids) domains of ICAm-1, as shown in FIG. 3.

ICAM-1 cDNA Clones

A plurality of methods may be used to clone genes. One method is to use two partially overlapping 47 mer oligonucleotide probes. These two probes termed oligonucleotide ICAM-1 and oligonucleotide ICAM-3 were synthesized from the published ICAM-1 sequence. The ICAM-1 oligonucleotide was labeled to high specific activity and hybridized to a Southern blot under high stringency conditions. As shown in FIG. 4A, a single band of 4.4 kb was detected in HeLa, HE1 and two primary HRR transfectant cell lines and was absent from Ltk⁻ cells. This result confirms that the HRR transfectants contain the human ICAM-1 gene. The size of the fragment agrees with Simmons et al but differs from Staunton et al probably reflecting a restriction site polymorphism.

The ICAM-1 oligonucleotide was used to probe a Northern blot of poly A+ RNA from the same cell lines. As shown in FIG. 4B, an mRNA of 3.3 kb was detected in HeLa, HE1, and primary transfectant cell lines but was absent from Ltk⁻ cells. The signal in HE1 cells was many times stronger than the other cell lines indicating a much higher level of MRNA in HE1 cells. This is in agreement with the higher level of HRR (ICAM-1) expression in HE1 cells. A second 2.4 kb RNA was also detected in HE1 cells. These data confirm that the human ICAM-1 MRNA is expressed in HRR transfectants. See FIG. 4B.

The human ICAM-1 gene was isolated from the HE1 transfectant using polymerase chain reaction (PCR) amplification utilizing the Perkin-Elmer/Cetus DNA Amplification System, Perkin Elmer, Wellesley Mass. PCR amplification was performed on single stranded cDNA made from HeLa, Ltd⁻ and HE1 RNA. Primers were made from the 5' and 3' coding regions of the published ICAM-1 sequence. ICAM-1 specific amplification products were detected by hybridization of a Southern blot of the PCR reactions using the ICAM-1 oligonucleotide. As shown in FIG. 4C, a single band of approximately 1600 bp which matches the predicted size was amplified from HeLa cells and HE1 cells but was absent from Ltk⁻ cells. The amplification product was cloned into Bluescript® (Strategene, San Diego, Calif.) and two independent clones designated PHRR1 and PHRR2 were obtained. The complete sequence of PHRR2 showed 100% identity with the published ICAM-1 coding sequence with the exception of a single G to A change previously described.

A lambda GT11 library made from randomly primed HE1 cDNA was screened with the ICAM-1 and ICAM-3 probes and eight positive clones were isolated. Six clones as shown in FIG. 7 were selected for further study and were anlayzed by partial DNA sequencing. A total of approximately 1000 nucleotides of sequence derived from these clones showed identity with the ICAM-1 sequence.

Purification and Isolation of Soluble Protein HeLa and HE1 cells are grown under standard conditions in DMEM (Dulbecco's Modified Essential Media) with 10% Fetal Bovine Serum. Conditioned media from these cells is harvested and centrifuged or filtered to remove cells or cellular debris. The cell-membrane bound ICAM-1 is not present in the supernatant. This media is then absorbed to a monoclonal antibody-sepharose resin (the monoclonal antibody c78.4 A being an example) in which the monoclonal antibody is directed to ICAM-1 or sICAM-1 and the unabsorbed proteins are washed from the resin with a physiological saline buffer, such as phosphate-buffered saline. The bound sICAM-1 is then eluted under conditions that preserve the native conformation of the protein, as described in copending application Ser. No. 262428 filed Oct. 25, 1988. The sICAM-1 may be further purified by lectin affinity chromatography, ion exchange chromatography, or gel filtration.

mRNA transcribed in vitro from cDNA encoding sICAM in the Bluescript® vector (Strategene) was translated in vitro. In the absence of microsomal membranes, an unglycosylated protein with an apparent MW of 52,000 daltons was obtained; in the presence of microsomal membranes, a glycosylated species of 72,400 daltons was obtained which was sequestered within the microsomal membrane, indicating that the sICAM polypeptide is correctly translocated, processed, and glycosylated by the microsomal membranes.

cDNA's encoding tmICAM and sICAM in the CDM8 vector (See, B. and Aruffo, A. PNAS 84:3365 (1987) were transfected into COS cells and mouse L cells using the DEAE-dextran technique. AT 72 hr, the cells were analyzed by two methods: (1) FACS analysis with anti-ICAM Mab (c78.4) for cell membrane expression of ICAM species and (2) metabolic labeling followed by immunoabsorption with anti-ICAM Mab of cell supernatants and cell lysates. The results from the metabolic labelling indicated intracellular accumulation of a 68,000 dalton species in sICAM-transfected cells but no detectable secretion of sICAM into th supernatant. These data are consistent with sICAM being secreted through the "Regulated" secretory pathway (R. B. Kelly, Science 230:25 (1985)).

Antibody probes specific for sICAM and for ICAM-1 were prepared. The synthetic peptides S-PEP,
P P G M R L S S S L W (C)[SEQ ID NO: 8]
derived from a unique 11 amino acid sequence at the C-terminus of sICAM, and P002, derived from the C-terminus of ICAM-1,
G T P M K P N T Q A T P P (C)SEQ ID NO: 8
was made and purified; the C-terminal C residues in parentheses were added to facilitate coupling of the peptides to protein carriers. The synthetic peptide was coupled to KLH (Keyhole Limpit Hemocyanin) by standard procedures and the conjugate injected into rabbits to product anti-peptide antisera were shown to specifically bind to their respective peptide immunogens.

What is claimed is:

1. An antibody which binds to sICAM-1 having the amino acid sequence shown in FIG. 1 and does not bind to insoluble ICAM-1.

2. The antibody of claim 1 wherein said antibody is a polyclonal antibody.

3. The antibody of claim 1 capable of binding to the amino acid sequence PPGMRLSSSLW.

4. A hybridoma cell line capable of producing the monoclonal antibody of claim 1.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: no ( i x ) FEATURE:
    ( A ) NAME/KEY: PCR 5.1 (5'PCR primer)
    ( B ) LOCATION: 5'end of ICAM-1 coding sequence
    ( D ) OTHER INFORMATION: bp 1 = G; bp 2-7 = EcoRI
        site; bp 8- 31 = 24 bases coding for the first
        eight amino acid residues of hICAM-1

( x ) PUBLICATION INFORMATION:
    ( A ) AUTHORS: Greve, J.M., G. Davis, A.M. Meyer,
        C.P. Forte, S.C. Yost, C.W. Marlor, M.E.
        Kamarck, and A. McClelland
    ( B ) TITLE: The Major Human Rhinovirus Receptor is
        ICAM-1
    ( C ) JOURNAL: Cell
    ( D ) VOLUME: 56
    ( F ) PAGES: 839-847
    ( G ) DATE: March 10, 1989
    ( K ) RELEVANT RESIDUES IN SEQ ID NO:1: FROM 1 TO
        31

( x i ) SEQUENCE DESCRIPTION: SEQ ID NO:1:

```
GGAATTC ATG GCT CCC AGC AGC CCC CGG CCC                    3 1
        Met Ala Pro Ser Ser Pro Arg Pro
                         5
```

( 2 ) INFORMATION FOR SEQ ID NO:2:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( i x ) FEATURE:
        ( A ) NAME/KEY: PCR 3.1 (3'PCR primer)
        ( B ) LOCATION: 3'end of ICAM-1 coding sequence
        ( D ) OTHER INFORMATION: base 1 =G; base 2-7 =
            EcoRI site; base 8-31 = 24 bases
            complementary to nucleic acid sequence coding
            for last 8 amino acid residues of hICAM-1

( x ) PUBLICATION INFORMATION:
        ( A ) AUTHORS: Greve, J.M., G. Davis, A.M. Meyer,
            C.P. Forte, S.C. Yost, C.W. Marlor, M.E.
            Kamarck, and A. McClelland
        ( B ) TITLE: The Major Human Rhinovirus Receptor is
            ICAM-1
        ( C ) JOURNAL: Cell
        ( D ) VOLUME: 56
        ( F ) PAGES: 839-847
        ( G ) DATE: March 10, 1989
        ( K ) RELEVANT RESIDUES IN SEQ ID NO:2: FROM 1 TO
            31

( x i ) SEQUENCE DESCRIPTION: SEQ ID NO:2:

```
GGAATTCTCA GGGAGGCGTG GCTTGTGTGT T                          3 1
```

( 2 ) INFORMATION FOR SEQ ID NO:3:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: no ( i x ) FEATURE:
    ( A ) NAME/KEY: PCR 5.4 (5'PCR primer)
    ( B ) LOCATION: nucleotides 1351 to 1374 of sICAM ( x i ) SEQUENCE DESCRIPTION: SEQ ID NO:3:

```
CTT  GAG  GGC  ACC  TAC  CTC  TGT  CGG                    24
Leu  Glu  Gly  Thr  Tyr  Leu  Cys  Arg
                    5
```

( 2 ) INFORMATION FOR SEQ ID NO:4:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( i x ) FEATURE:
        ( A ) NAME/KEY: 3'PCR primer
        ( B ) LOCATION: complementary to nucleotides 1432 -
            1455 of sICAM ( x i ) SEQUENCE DESCRIPTION: SEQ ID NO:4:

```
AGTGATGATG  ACAATCTCAT  ACCG                              24
```

( 2 ) INFORMATION FOR SEQ ID NO:5:

( i ) SEQUENCE CHARACTERISTICS:
        ( A ) LENGTH: 47 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( i x ) FEATURE:
        ( A ) NAME/KEY: ICAM1 probe
        ( B ) LOCATION: complementary to nucleotides 565 to
            611 of ICAM- 1

( x ) PUBLICATION INFORMATION:
        ( A ) AUTHORS: Greve, J.M., G. Davis, A.M. Meyer,
            C.P. Forte, S.C. Yost, C.W. Marlor, M.E.
            Kamarck, and A. McClelland
        ( B ) TITLE: The Major Human Rhinovirus Receptor is
            ICAM-1
        ( C ) JOURNAL: Cell
        ( D ) VOLUME: 56
        ( F ) PAGES: 839-847
        ( G ) DATE: March 10, 1989
        ( K ) RELEVANT RESIDUES IN SEQ ID NO:5: FROM 1 TO
            47

( x i ) SEQUENCE DESCRIPTION: SEQ ID NO:5:

```
GAGGTGTTCT  CAAACAGCTC  CAGCCCTTGG  GGCCGCAGGT  CCAGTTC    47
```

( 2 ) INFORMATION FOR SEQ ID NO:6:

( i ) SEQUENCE CHARACTERISTICS:
        ( A ) LENGTH: 47 bases
        ( B ) TYPE: nucleic acid ( C ) STRANDEDNESS: single
              ( D ) TOPOLOGY: linear ( i i ) MOLECULE TYPE: other nucleic acid ( i i i ) HYPOTHETICAL: no ( i v ) ANTI-SENSE: yes ( i x ) FEATURE:
              ( A ) NAME/KEY: ICAM3 probe
              ( B ) LOCATION: complementary to nucleotides 602 to
                    648 of human ICAM ( x ) PUBLICATION INFORMATION:
              ( A ) AUTHORS: Greve, J.M., G. Davis, A.M. Meyer,
                    C.P. Forte, S.C. Yost, C.W. Marlor, M.E.
                    Kamarck, and A. McClelland
              ( B ) TITLE: The Major Human Rhinovirus Receptor is
                    ICAM-1
              ( C ) JOURNAL: Cell
              ( D ) VOLUME: 56
              ( F ) PAGES: 839-847
              ( G ) DATE: March 10, 1989
              ( K ) RELEVANT RESIDUES IN SEQ ID NO:6: FROM 1 TO
                    47

( x i ) SEQUENCE DESCRIPTION: SEQ ID NO:6:

CGTTGGCAGG ACAAAGGTCT GGAGCTGGTA GGGGGCCGAG GTGTTCT                                47

( 2 ) INFORMATION FOR SEQ ID NO:7:

( i ) SEQUENCE CHARACTERISTICS:
              ( A ) LENGTH: 34 bases
              ( B ) TYPE: nucleic acid
              ( C ) STRANDEDNESS: single
              ( D ) TOPOLOGY: linear ( i i ) MOLECULE TYPE: other nucleic acid ( i i i ) HYPOTHETICAL: no ( i v ) ANTI-SENSE: yes ( i x ) FEATURE:
              ( A ) NAME/KEY: PCR 3.2 antisense
              ( D ) OTHER INFORMATION: base 1 =G; bases 2-7 =
                    EcoR1 site; bases 8-10 = complementary to a stop
                    codon; bases 11-34 = 24 bases complementary to
                    nucleotides 1474-1497 of ICAM-1, nucleotide 1 being
                    the ATG ( x i ) SEQUENCE DESCRIPTION: SEQ ID NO:7:

GGAATTCTCA CTCATACCGG GGGGAGAGCA CATT                                             34

( 2 ) INFORMATION FOR SEQ ID NO:8:

( i ) SEQUENCE CHARACTERISTICS:
              ( A ) LENGTH: 12 amino acid residues
              ( B ) TYPE: amino acid
              ( D ) TOPOLOGY: linear ( i i ) MOLECULE TYPE:
              ( A ) DESCRIPTION: peptide ( i i i ) HYPOTHETICAL: no ( v ) FRAGMENT TYPE: modified C-terminal fragment ( i x ) FEATURE:
              ( A ) NAME/KEY: modified sICAM fragment
              ( B ) LOCATION: C-terminus of sICAM
              ( D ) OTHER INFORMATION: first 11 amino acids
                    correspond to C-terminus of sICAM; last
                    residue (Cys) added to faciliate coupling ( x i ) SEQUENCE DESCRIPTION: SEQ ID NO:8:

| Pro | Pro | Gly | Met | Arg | Leu | Ser | Ser | Ser | Leu | Trp | Cys |
|---|---|---|---|---|---|---|---|---|---|---|---|
|   |   |   |   | 5 |   |   |   |   | 10 |   |   |

( 2 ) INFORMATION FOR SEQ ID NO:9:

( i ) SEQUENCE CHARACTERISTICS:
        ( A ) LENGTH: 14 amino acid residues
        ( B ) TYPE: amino acid
        ( D ) TOPOLOGY: linear ( i i ) MOLECULE TYPE:
        ( A ) DESCRIPTION: peptide ( i i i ) HYPOTHETICAL: no ( v ) FRAGMENT TYPE: C-terminal fragment ( i x ) FEATURE:
        ( A ) NAME/KEY: modified ICAM fragment
        ( B ) LOCATION: C-terminus
        ( D ) OTHER INFORMATION: first 11 amino acid
            residues correspond to the C-terminus of
            ICAM; last residue (Cys) added to faciliate
            coupling ( x i ) SEQUENCE DESCRIPTION: SEQ ID NO:9:

| Gly | Thr | Pro | Met | Lys | Pro | Asn | Thr | Gln | Ala | Thr | Pro | Pro | Cys |
|---|---|---|---|---|---|---|---|---|---|---|---|---|---|
|   |   |   |   | 5 |   |   |   |   | 10 |   |   |   |   |

( 2 ) INFORMATION FOR SEQ ID NO:10:

( i ) SEQUENCE CHARACTERISTICS:
        ( A ) LENGTH: 1443 bases
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: human
        ( G ) CELL TYPE: epithelial
        ( H ) CELL LINE: HeLa ( v i i ) IMMEDIATE SOURCE:
        ( A ) LIBRARY: cDNA library ( i x ) FEATURE:
        ( A ) NAME/KEY: human sICAM cDNA to mRNA sequence
        ( B ) LOCATION: nucleotides 1 to 1435 numbered
            beginning at ATG coding for first Met of
            human sICAM protein ( x i ) SEQUENCE DESCRIPTION: SEQ ID NO:10:

| ATG | GCT | CCC | AGC | AGC | CCC | CGG | CCC | GCG | CTG | CCC | GCA | CTC | CTG | GTC | 45 |
|---|---|---|---|---|---|---|---|---|---|---|---|---|---|---|---|
| Met | Ala | Pro | Ser | Ser | Pro | Arg | Pro | Ala | Leu | Pro | Ala | Leu | Leu | Val |  |
|   |   |   |   | 5 |   |   |   |   | 10 |   |   |   |   | 15 |  |

| CTG | CTC | GGG | GCT | CTG | TTC | CCA | GGA | CCT | GGC | AAT | GCC | CAG | ACA | TCT | 90 |
|---|---|---|---|---|---|---|---|---|---|---|---|---|---|---|---|
| Leu | Leu | Gly | Ala | Leu | Phe | Pro | Gly | Pro | Gly | Asn | Ala | Gln | Thr | Ser |  |
|   |   |   |   | 20 |   |   |   |   | 25 |   |   |   |   | 30 |  |

| GTG | TCC | CCC | TCA | AAA | GTC | ATC | CTG | CCC | CGG | GGA | GGC | TCC | GTG | CTG | 135 |
|---|---|---|---|---|---|---|---|---|---|---|---|---|---|---|---|
| Val | Ser | Pro | Ser | Lys | Val | Ile | Leu | Pro | Arg | Gly | Gly | Ser | Val | Leu |  |
|   |   |   |   | 35 |   |   |   |   | 40 |   |   |   |   | 45 |  |

| GTG | ACA | TGC | AGC | ACC | TCC | TGT | GAC | CAG | CCC | AAG | TTG | TTG | GGC | ATA | 180 |
|---|---|---|---|---|---|---|---|---|---|---|---|---|---|---|---|
| Val | Thr | Cys | Ser | Thr | Ser | Cys | Asp | Gln | Pro | Lys | Leu | Leu | Gly | Ile |  |
|   |   |   |   | 50 |   |   |   |   | 55 |   |   |   |   | 60 |  |

-continued

```
GAG ACC CCG TTG CCT AAA AAG GAG TTG CTC CTG CCT GGG AAC AAC            225
Glu Thr Pro Leu Pro Lys Lys Glu Leu Leu Leu Pro Gly Asn Asn
             65                  70                  75

CGG AAG GTG TAT GAA CTG AGC AAT GTG CAA GAA GAT AGC CAA CCA            270
Arg Lys Val Tyr Glu Leu Ser Asn Val Gln Glu Asp Ser Gln Pro
                 80                  85                  90

ATG TGC TAT TCA AAC TGC CCT GAT GGG CAG TCA ACA GCT AAA ACC            315
Met Cys Tyr Ser Asn Cys Pro Asp Gly Gln Ser Thr Ala Lys Thr
                 95                 100                 105

TTC CTC ACC GTG TAC TGG ACT CCA GAA CGG GTG GAA CTG GCA CCC            360
Phe Leu Thr Val Tyr Trp Thr Pro Glu Arg Val Glu Leu Ala Pro
                110                 115                 120

CTC CCC TCT TGG CAG CCA GTG GGC AAG AAC CTT ACC CTA CGC TGC            405
Leu Pro Ser Trp Gln Pro Val Gly Lys Asn Leu Thr Leu Arg Cys
                125                 130                 135

CAG GTG GAG GGT GGG GCA CCC CGG GCC AAC CTC ACC GTG GTG CTG            450
Gln Val Glu Gly Gly Ala Pro Arg Ala Asn Leu Thr Val Val Leu
                140                 145                 150

CTC CGT GGG GAG AAG GAG CTG AAA CGG GAG CCA GCT GTG GGG GAG            495
Leu Arg Gly Glu Lys Glu Leu Lys Arg Glu Pro Ala Val Gly Glu
                155                 160                 165

CCC GCT GAG GTC ACG ACC ACG GTG CTG GTG AGG AGA GAT CAC CAT            540
Pro Ala Glu Val Thr Thr Thr Val Leu Val Arg Arg Asp His His
                170                 175                 180

GGA GCC AAT TTC TCG TGC CGC ACT GAA CTG GAC CTG CGG CCC CAA            585
Gly Ala Asn Phe Ser Cys Arg Thr Glu Leu Asp Leu Arg Pro Gln
                185                 190                 195

GGG CTG GAG CTG TTT GAG AAC ACC TCG GCC CCC TAC CAG CTC CAG            630
Gly Leu Glu Leu Phe Glu Asn Thr Ser Ala Pro Tyr Gln Leu Gln
                200                 205                 210

ACC TTT GTC CTG CCA GCG ACT CCC CAA CTT GTC AGC CCC CGG            675
Thr Phe Val Leu Pro Ala Thr Pro Pro Gln Leu Val Ser Pro Arg
                215                 220                 225

GTC CTA GAG GTG GAC ACG CAG GGG ACC GTG GTC TGT TCC CTG GAC            720
Val Leu Glu Val Asp Thr Gln Gly Thr Val Val Cys Ser Leu Asp
                230                 235                 240

GGG CTG TTC CCA GTC TCG GAG GCC CAG GTC CAC CTG GCA CTG GGG            765
Gly Leu Phe Pro Val Ser Glu Ala Gln Val His Leu Ala Leu Gly
                245                 250                 255

GAC CAG AGG TTG AAC CCC ACA GTC ACC TAT GGC AAC GAC TCC TTC            810
Asp Gln Arg Leu Asn Pro Thr Val Thr Tyr Gly Asn Asp Ser Phe
                260                 265                 270

TCG GCC AAG GCC TCA GTC AGT GTG ACC GCA GAG GAC GAG GGC ACC            855
Ser Ala Lys Ala Ser Val Ser Val Thr Ala Glu Asp Glu Gly Thr
                275                 280                 285

CAG CGG CTG ACG TGT GCA GTA ATA CTG GGG AAC CAG AGC CAG GAG            900
Gln Arg Leu Thr Cys Ala Val Ile Leu Gly Asn Gln Ser Gln Glu
                290                 295                 300

ACA CTG CAG ACA GTG ACC ATC TAC AGC TTT CCG GCG CCC AAC GTG            945
Thr Leu Gln Thr Val Thr Ile Tyr Ser Phe Pro Ala Pro Asn Val
                305                 310                 315

ATT CTG ACG AAG CCA GAG GTC TCA GAA GGG ACC GAG GTG ACA GTG            990
Ile Leu Thr Lys Pro Glu Val Ser Glu Gly Thr Glu Val Thr Val
                320                 325                 330

AAG TGT GAG GCC CAC CCT AGA GCC AAG GTG ACG CTG AAT GGG GTT           1035
Lys Cys Glu Ala His Pro Arg Ala Lys Val Thr Leu Asn Gly Val
                335                 340                 345

CCA GCC CAG CCA CTG GGC CCG AGG GCC CAG CTC CTG CTG AAG GCC           1080
Pro Ala Gln Pro Leu Gly Pro Arg Ala Gln Leu Leu Leu Lys Ala
                350                 355                 360
```

| | | | | | | | | | | | | | | | |
|---|---|---|---|---|---|---|---|---|---|---|---|---|---|---|---|
| ACC | CCA | GAG | GAC | AAC | GGG | CGC | AGC | TTC | TCC | TGC | TCT | GCA | ACC | CTG | 1125 |
| Thr | Pro | Glu | Asp | Asn | Gly | Arg | Ser | Phe | Ser | Cys | Ser | Ala | Thr | Leu | |
| | | | | 365 | | | | 370 | | | | | | 375 | |
| GAG | GTG | GCC | GGC | CAG | CTT | ATA | CAC | AAG | AAC | CAG | ACC | CGG | GAG | CTT | 1170 |
| Glu | Val | Ala | Gly | Gln | Leu | Ile | His | Lys | Asn | Gln | Thr | Arg | Glu | Leu | |
| | | | | 380 | | | | 385 | | | | | | 390 | |
| CGT | GTC | CTG | TAT | GGC | CCC | CGA | CTG | GAC | GAG | AGG | GAT | TGT | CCG | GGA | 1215 |
| Arg | Val | Leu | Tyr | Gly | Pro | Arg | Leu | Asp | Glu | Arg | Glu | Cys | Pro | Gly | |
| | | | | 395 | | | | 400 | | | | | | 405 | |
| AAC | TGG | ACG | TGG | CCA | GAA | AAT | TCC | CAG | CAG | ACT | CCA | ATG | TGC | CAG | 1260 |
| Asn | Trp | Thr | Trp | Pro | Glu | Asn | Ser | Gln | Gln | Thr | Pro | Met | Cys | Gln | |
| | | | | 410 | | | | 415 | | | | | | 420 | |
| GCT | TGG | GGG | AAC | CCA | TTG | CCC | GAG | CTC | AAG | TGT | CTA | AAG | GAT | GGC | 1305 |
| Ala | Trp | Gly | Asn | Pro | Leu | Pro | Glu | Leu | Lys | Cys | Leu | Lys | Asp | Gly | |
| | | | | 425 | | | | 430 | | | | | | 435 | |
| ACT | TTC | CCA | CTG | CCC | ATC | GGG | GAA | TCA | GTG | ACT | GTC | ACT | CGA | GAT | 1350 |
| Thr | Phe | Pro | Leu | Pro | Ile | Gly | Glu | Ser | Val | Thr | Val | Thr | Arg | Asp | |
| | | | | 440 | | | | 445 | | | | | | 450 | |
| CTT | GAG | GGC | ACC | TAC | CTC | TGT | CGG | GCC | AGG | AGC | ACT | CAA | GGG | GAG | 1395 |
| Leu | Glu | Gly | Thr | Tyr | Leu | Cys | Arg | Ala | Arg | Ser | Thr | Gln | Gly | Glu | |
| | | | | 455 | | | | 460 | | | | | | 465 | |
| GTC | ACC | CGC | AAG | CCC | CCC | GGT | ATG | AGA | TTG | TCA | TCA | TCA | CTG | TGG | 1440 |
| Val | Thr | Arg | Lys | Pro | Pro | Gly | Met | Arg | Leu | Ser | Ser | Ser | Leu | Trp | |
| | | | | 470 | | | | 475 | | | | | | 480 | |
| TAG | | | | | | | | | | | | | | | 1443 |

( 2 ) INFORMATION FOR SEQ ID NO:11:

( i ) SEQUENCE CHARACTERISTICS:
        ( A ) LENGTH: 240 bases
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: human
        ( G ) CELL TYPE: epithelial
        ( H ) CELL LINE: HeLa ( v i i ) IMMEDIATE SOURCE:
        ( A ) LIBRARY: cDNA library ( i x ) FEATURE:
        ( A ) NAME/KEY: partial human ICAM cDNA to mRNA
            sequence
        ( B ) LOCATION: nucleotides 1384 to 1623 numbered
            beginning at ATG coding for first Met of
            human ICAM protein ( x ) PUBLICATION INFORMATION:
        ( A ) AUTHORS: Greve, J.M., G. Davis, A.M. Meyer,
            C.P. Forte, S.C. Yost, C.W. Marlor, M.E.
            Kamarck, and A. McClelland
        ( B ) TITLE: The Major Human Rhinovirus Receptor is
            ICAM-1
        ( C ) JOURNAL: Cell
        ( D ) VOLUME: 56
        ( F ) PAGES: 839-847
        ( G ) DATE: March 10, 1989
        ( K ) RELEVANT RESIDUES IN SEQ ID NO:11: FROM 1 TO
            240

( x i ) SEQUENCE DESCRIPTION: SEQ ID NO:11:

| | | | | | | | | | | | | | | | |
|---|---|---|---|---|---|---|---|---|---|---|---|---|---|---|---|
| ACT | CAA | GGG | GAG | GTC | ACC | CGC | AAG | GTG | ACC | GTG | AAT | GTG | CTC | TCC | 45 |

```
Thr  Gln  Gly  Glu  Val  Thr  Arg  Lys  Val  Thr  Val  Asn  Val  Leu  Ser
                    5                         10                       15

CCC  CGG  TAT  GAG  ATT  GTC  ATC  ATC  ACT  GTG  GTA  GCA  GCC  GCA  GTC          90
Pro  Arg  Tyr  Glu  Ile  Val  Ile  Ile  Thr  Val  Val  Ala  Ala  Ala  Val
                    20                        25                       30

ATA  ATG  GGC  ACT  GCA  GGC  CTC  AGC  ACG  TAC  CTC  TAT  AAC  CGC  CAG         135
Ile  Met  Gly  Thr  Ala  Gly  Leu  Ser  Thr  Tyr  Leu  Tyr  Asn  Arg  Gln
                    35                        40                       45

CGG  AAG  ATC  AAG  AAA  TAC  AGA  CTA  CAA  CAG  GCC  CAA  AAA  GGG  ACC         180
Arg  Lys  Ile  Lys  Lys  Tyr  Arg  Leu  Gln  Gln  Ala  Gln  Lys  Gly  Thr
                    50                        55                       60

CCC  ATG  AAA  CCG  AAC  ACA  CAA  GCC  ACG  CCT  CCC  TGAACCTATC                  223
Pro  Met  Lys  Pro  Asn  Thr  Gln  Ala  Thr  Pro  Pro
                    65                        70

CCGGGACAGG  GCCTCTT                                                                240
```

( 2 ) INFORMATION FOR SEQ ID NO:12:

( i ) SEQUENCE CHARACTERISTICS:
        ( A ) LENGTH: 221 bases
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: human
        ( G ) CELL TYPE: epithelial
        ( H ) CELL LINE: HeLa ( v i i ) IMMEDIATE SOURCE:
        ( A ) LIBRARY: cDNA library ( i x ) FEATURE:
        ( A ) NAME/KEY: partial human sICAM-1 cDNA to mRNA
            sequence
        ( B ) LOCATION: sequence from human sICAM
            corresponding to nucleotides 1384 to 1623 of
            human ICAM lacking bp 1407 to 1426,
            inclusive, of hICAM ( x i ) SEQUENCE DESCRIPTION: SEQ ID NO:12:

```
ACT  CAA  GGG  GAG  GTC  ACC  CGC  AAG  CCC  CCC  GGT  ATG  AGA  TTG  TCA          45
Thr  Gln  Gly  Glu  Val  Thr  Arg  Lys  Pro  Pro  Gly  Met  Arg  Leu  Ser
                    5                         10                       15

TCA  TCA  CTG  TGG  TAGCAGCCGC  AGTCATAATG  GGCACTGCAG  GCCTCAGCAC                  97
Ser  Ser  Leu  Trp
GTACCTCTAT  AACCGCCAGC  GGAAGATCAA  GAAATACAGA  CTACAACAGG                          147

CCCAAAAAGG  GACCCCCATG  AAACCGAACA  CACAAGCCAC  GCCTCCCTGA                          197

ACCTATCCCG  GGACAGGGCC  TCTT                                                        221
```